United States Patent [19]

Nakamura et al.

[11] Patent Number: 4,691,070

[45] Date of Patent: Sep. 1, 1987

[54] CATALYST, ITS METHOD OF PREPARATION AND PROCESS FOR ITS USE IN THE HYDROGENATION OF DIOLEFINS

[75] Inventors: Teiji Nakamura; Eiichiro Nishikawa, both of Saitama; Takeo Koyama, Kanagawa, all of Japan

[73] Assignee: Toa Nenryo Kogyo Kabushiki Kaisha, Tokyo, Japan

[21] Appl. No.: 932,644

[22] Filed: Nov. 20, 1986

Related U.S. Application Data

[63] Continuation of Ser. No. 750,367, Jun. 28, 1985, abandoned.

[30] Foreign Application Priority Data

Jun. 28, 1984 [JP] Japan ............................ 59-131930

[51] Int. Cl.$^4$ ............................................ C07C 5/05
[52] U.S. Cl. ........................... 585/273; 585/259; 585/260; 585/261; 585/262
[58] Field of Search ............... 585/258, 259, 260, 261, 585/262, 263, 273

[56] References Cited

U.S. PATENT DOCUMENTS

| | | | |
|---|---|---|---|
| 2,927,141 | 3/1960 | Cohn et al. | 585/262 |
| 3,494,859 | 2/1970 | Parker | 585/261 |
| 3,787,514 | 1/1974 | Berausset | 585/262 |
| 3,909,456 | 9/1975 | Numagami et al. | 585/261 |
| 3,949,011 | 4/1976 | Smirnov et al. | 585/261 |
| 4,152,365 | 5/1979 | Drehman | 585/256 |
| 4,396,539 | 8/1983 | Sapienza et al. | 585/261 |
| 4,427,536 | 1/1984 | Klassen et al. | 208/113 |
| 4,431,750 | 2/1984 | McGinnis et al. | 502/329 |
| 4,492,769 | 1/1985 | Blanchard et al. | 502/262 |

FOREIGN PATENT DOCUMENTS

| | | | |
|---|---|---|---|
| 1237412 | 6/1960 | France | 585/260 |
| 1580556 | 9/1969 | France | 585/260 |
| 811820 | 4/1959 | United Kingdom | 585/260 |
| 866395 | 4/1961 | United Kingdom | 585/260 |
| 1387385 | 3/1975 | United Kingdom | 585/261 |

*Primary Examiner*—Asok Pal
*Attorney, Agent, or Firm*—J. J. Mahon

[57] ABSTRACT

A catalyst for the hydrogenation of a diolefin, having palladium or a compound thereof and at least one co-catalyst component selected from the group consisting of ruthenium, rhodium, cobalt, and rhenium supported each in the form of an elemental metal or a metal compound on a support, its method of preparation and its use for said hydrogenation, particularly for the hydrogenation of cyclopentadiene to cyclopentene is described herein.

6 Claims, No Drawings

ND PROCESS FOR ITS USE IN THE
CATALYST, ITS METHOD OF PREPARATION AND PROCESS FOR ITS USE IN THE HYDROGENATION OF DIOLEFINS

This is a continuation of application Ser. No. 750,367, filed 6/28/85, now abandoned.

This invention relates to a catalyst for the hydrogenation of a diolefin, which catalyst contains palladium and at least one element selected from the group consisting of ruthenium, rhodium, cobalt, and rhenium carried each in the form of an elemental metal or a metal compound on a support and which excels in activity and selectivity.

BACKGROUND OF THE INVENTION

Heretofore, palladium-containing catalysts have found considerable utility in commercial applications because they exhibit sufficient activity in thorough hydrogenation of unsaturated hydrocarbon compounds and retain this activity intact over protracted use. It is known, however, that for the purpose of partial (selective) hydrogenation of diolefins, these catalysts are used as combined or alloyed with some other metals because they exhibit excessive activity and insufficient selectivity. Examples of such a deficiency is seen in a method for the production of cyclopentene by the partial hydrogenation of cyclopentadiene by the use of a catalyst having palladium and iron carried on alumina or magnesium oxide (Japanese Patent Publication SHOWA 52[1977]-33,627 and Japanese Patent Application Laid-open SHOWA 49[1974]-88,837) and in a method for the production of a cyclic olefin by the hydrogenation of a cyclic diene by the use of a palladium-ruthenium alloy having a ruthenium content of 1 to 11% by weight or a palladium-rhodium alloy having a rhodium content of 1 to 5% by weight as a catalyst (Japanese Patent Publication SHOWA 53[1978]-24,938).

The method which uses a supported catalyst of palladium and iron, however, is such that the catalyst used therein has insufficient activity and selectivity, although it is improved in selectivity over a supported catalyst exclusively of palladium. Then, the method which uses the palladium-ruthenium alloy or the palladium-rhodium alloy as a catalyst is such that the catalyst used therein exhibits lower activity than the supported catalyst and entails the problem that it acquires improvement in activity at a sacrifice of selectivity.

It is an object of this invention to overcome the disadvantages as described above in the conventional production of monoolefins by the partial hydrogenation of diolefins.

SUMMARY OF THE INVENTION

The catalyst of the present invention for the hydrogenation of a diolefin comprises from 0.01 to 10% by weight of palladium and at least one co-catalyst compound in the form of an element selected from the group consisting of ruthenium, rhodium, cobalt, and rhenium carried each in the form of an elemental metal or a metal compound on a support. The process of the invention involves making the catalyst described above comprising the step of depositing from 0.01 to 10% by weight of palladium or its compounds and from 0.01 to 5% by weight of at least one element selected from the group consisting of ruthenium, rhodium, cobalt, rhenium and compounds thereof on a support, said weight percent based on the total weight of the catalyst and support and support.

The invention is also concerned with the production of a monoolefin by the partial hydrogenation of a corresponding diolefin which hydrogenation is carried out in the presence of the above described catalyst.

DETAILED DESCRIPTION OF THE INVENTION

The support to be used in this invention is an inorganic compound which preferably has a surface area of not more than 100 $m^2/g$ and is of a non-acid type. Examples of the support include magnesium-supported alpha-alumina, alpha-alumina, lithium/aluminum spinel, and magnesium oxide. The magnesium-supported alpha-alumina is the best selection.

The compounds of palladium and metals of ruthenium, rhodium, cobalt, and rhenium embrace halides, nitrates, sulfates, hydroxides, oxides, carboxylates, etc. of the metal elements. Of the metal compounds enumerated above, such chlorides as palladium chloride, ruthenium chloride, rhodium chloride, cobalt chloride, and rhenium chloride are particularly desirable.

The deposition of the catalyst component on the carrier is effected by dissolving the metals and/or metal compounds of the catalyst components in water, hydrochloric acid, nitric acid, an acid aqueous solution, an alkali aqueous solution, or an organic solvent such as alcohol, ketone, ether, aliphatic carboxylic acid, or ester, immersing the support in the resultant solution thereby allowing the metal compound to be adsorbed on the support, thermally vaporizing the solution thereby expelling the solvent or removing excess solution by decantation or filtration, optionally washing the residue with water, drying the cleaned residue, and reducing it. The catalyst components may be dissolved and deposited together or deposited sequentially.

The catalyst components to be carried are the combination of (1) a palladium component and (2) at least one component selected from the group consisting of ruthenium, rhodium, cobalt, and rhenium (hereinafter referred to as "co-catalyst"). Among them, the combination of palladium and ruthenium proves particularly desirable.

The amounts of the catalyst components to be supported are 0.01 to 10% by weight, preferably 0.05 to 2% by weight, of the palladium component as palladium metal and 0.01 to 5% by weight, preferably 0.05 to 1% by weight, of the co-catalyst component as co-catalyst metal, both based on the total weight of the supported catalyst.

The weight ratio of the co-catalyst metal per weight part of the palladium metal in the supported catalyst is in the range of 0.14 to 5, preferably 0.4 to 1.

The support which has had the catalyst components adsorbed (deposited) thereon by the steps of immersing the support in the solution containing the compound of palladium and the compound of the co-catalyst component and then removing the solvent from the solution is subsequently dried at 100° to 300° C. for 1 to 24 hours. The resulting supported catalyst can be used directly in its unmodified form. It is, however, desired to be subjected to a reducing treatment preparatory to its actual use. The reduction can be effected by the use of hydrogen or hydrazine, for example.

The supported catalyst of palladium and co-catalyst according to the present invention can be used in the production of a monoolefin by the partial hydrogenation of a corresponding diolefin.

Examples of a diolefin suitable for the partial hydrogenation include acyclic diolefins such as 1,3-butadiene, 1,3-pentadiene, 2-methyl-1,3-butadiene, 2,3-dimethyl-1,3-butadiene, 1,3-hexadiene, 2,4-hexadiene, 1,3-octadiene, and 4-phenyl-1,3-butadiene, and cyclic diolefins such as cyclopentadiene, cyclohexadiene, and 1,3-cyclooctadiene. The catalyst of the invention is particularly suitable for the production of cyclopentene by the partial hydrogenation of cyclopentadiene.

The amount of hydrogen required to be present during the partial hydrogenation of the diolefin by the use of the catalyst of this invention has at least to equal the theoretical amount necessary for the conversion of the diolefin into the corresponding monoolefin through hydrogenation. Generally, the mol ratio of the diolefin to the molecular hydrogen falls in the range of 1/0.8 to 1.5, preferably 1/1.0 to 1.1. If the aforementioned mol ratio is less than 0.8, the conversion of the diolefin is not sufficient. If the mol ratio exceeds 1.5, the selectivity is insufficient. Any deviation of the mol ratio from the aforementioned range is undesirable.

The reaction temperature for the partial hydrogenation of the diolefin is in the range of 40° to 300° C., preferably 50° to 200° C. The reaction pressure is atmospheric pressure and higher pressures. The reaction can be carried out either continuously or batchwise in either a gaseous phase or a liquid phase. For the reaction in the liquid phase, the diolefin should be used in the form of a dilute solution to prevent the diolefin from dimerization. From the standpoint of the productivity of the reaction, the reaction is desired to be carried out continuously in the gaseous phase.

The proportions of the mixture of diolefin and hydrogen as raw materials and the catalyst are generally desired to be such that the contact time (volume of catalyst/volume of gas/second) will fall in the range of 0.1 to 10 seconds, preferable 0.1 to 5 seconds.

The supported catalyst of this invention, in the partial hydrogenation of a diolefin, produces a corresponding monoolefin with higher activity and higher selectivity than the conventional types of catalysts and, what is more, effects the reaction with a very short contact time.

The present invention is described below with working examples.

EXAMPLE 1

A palladium-ruthenium catalyst using magnesium-supported alpha-alumina as a support was prepared as follows.

Commercially available alpha-alumina in the amount of 200 g was impregnated with 250 ml of an aqueous solution containing 8.36 g of magnesium chloride MbCl$_2$.6H$_2$O), dried, then calcined at 600° C. for five hours to obtain a magnesium-supported alpha-alumina support (having a surface area of not more than 10 m$^2$/g).

The aforementioned support was impregnated with 200 ml of acetone solution containing 1.66 g of palladium chloride, 1.07 g of ruthenium chloride, and 40 ml of 35% hydrochloric acid and dried at 120° C. The dry composite was reduced with an aqueous solution containing 10% by weight of hydrazine and 10% by weight of sodium hydroxide for two hours, then washed with cold water until thorough removal of the chlorides, and dried at 120° C. for 12 hours. The supported catalyst so produced was found to contain 0.5% by weight of palladium and 0.2% of weight of ruthenium.

Cyclopentadiene prepared as described below was partially hydrogenated by the use of the aforementioned catalyst to produce cyclopentene.

Dicyclopentadiene, hydrogen gas, and nitrogen gas were introduced in respective flow volumes of 14.8 ml/min., 30 ml/min., and 30 ml/min. into a depolymerization bed packed with 35 ml of zinc oxide and heated at 320° C. to effect depolymerization of dicyclopentadiene into cyclopentadiene. The gas containing the produced cyclopentadiene was cooled to 40° to 50° C. to separate the unaltered dicyclopentadiene. In this case, the conversion by depolymerization was 98%.

A mixed gas consisting of 32.2% by volume (hereinafter abbreviated as "%") of the aforementioned depolymerized cyclopentadiene, 33.9% of hydrogen, and 33.9% of nitrogen (mol ratio of hydrogen/cyclopentadiene = 1.05) was introduced into a hydrogenation bed packed with 2 ml of the aforementioned palladium-ruthenium supported catalyst under the conditions of 99° C. of reaction temperature, atmospheric pressure, and 1.3 seconds of contact time. The reaction product was cooled and collected, and analyzed by gas chromatography. The results are shown in Table 1.

EXAMPLES 2–4

Catalysts were prepared by following the procedure of EXAMPLE 1, except that 1.78 g of rhodium chloride, 4.06 g of cobalt chloride, and 0.64 g of rhenium chloride were severally used in the place of ruthenium chloride. They were used in hydrogenation of cyclopentadiene. The results are shown in Table 1.

EXAMPLE 5

A catalyst was prepared by following the procedure of Example 1, except that an alpha-alumina was used as a support in the place of magnesium-supported alpha-alumina. This catalyst was used in hydrogenation of cyclopentadiene. The results are shown in Table 1.

EXAMPLE 7

A catalyst was prepared by following the procedure of Example 1, except that magnesium oxide (having a surface are of not more than 1 m$^2$/g) was used as the support in the place of magnesium-supported alpha-alumina. This catalyst was used in hydrogenation of cyclopentadiene. The results are shown in Table 1.

COMPARATIVE EXPERIMENT 1

A catalyst was prepared by following the procedure of Example 1, except that palladium chloride alone was used as a catalyst component. This catalyst was used in hydrogenation of cyclopentadiene. The results are shown in Table 1.

COMPARATIVE EXPERIMENT 2

The amount 33.6 g of magnesium oxide having a surface area of not more than 1 m$^2$/g was impregnated with 60 ml of an aqueous solution of 3.5% by weight of hydrochloric acid containing 0.25 g of palladium chloride and 0.36 g of ferrous chloride (FeCl$_2$.4H$_2$) and then drained. The resultant composite was reduced with an aqueous solution containing 10% by weight of sodium hydroxide and 10% by weight of hydrazine for two hours, washed with cold water until thorough removal of the chlorides, and dried in a vacuum drier at 150° C. for 12 hours. The catalyst so produced was found to contain 0.43 % by weight of palladium and 0.3% by weight of iron.

This catalyst was used in hydrogenation of cyclopentadiene after the procedure of Example 1. The results are shown in Table 1.

TABLE 1

| Example | Carried catalyst | | | | Reaction temperature (°C.) | Conversion (%) | Selectivity (%) |
| | Palladium content (wt %) | Co-catalyst | | Carrier | | | |
| | | Kind | Content (wt %) | | | | |
| --- | --- | --- | --- | --- | --- | --- | --- |
| Example 1 | 0.5 | Ruthenium | 0.2 | Mg/α-Al$_2$O$_3$ | 99 | 98.0 | 97.0 |
| 2 | 0.5 | Rhodium | 0.2 | " | 106 | 93.9 | 93.5 |
| 3 | 0.5 | Cobalt | 0.5 | " | 103 | 95.9 | 95.7 |
| 4 | 0.5 | Rhenium | 0.2 | " | 105 | 91.3 | 93.1 |
| 5 | 0.5 | Ruthenium | 0.2 | α-Al$_2$O$_3$ | 103 | 94.9 | 95.7 |
| 6 | 0.1 | Ruthenium | 0.04 | Mg/α-Al$_2$O$_3$ | 100 | 96.1 | 97.5 |
| 7 | 0.5 | Ruthenium | 0.2 | MgO | 100 | 95.3 | 95.0 |
| Comparative experiment 1 | 0.5 | — | — | Mg/αAl$_2$O$_3$ | 100 | 92.1 | 79.6 |
|  |  |  |  |  | 113 | 97.3 | 76.6 |
| 2 | 0.43 | Iron | 0.30 | MgO | 101 | 91.9 | 91.0 |

What is claimed is:

1. A method for the hydrogenation of a cyclic diolefin selected for the group consisting of cyclopentadiene, cyclohexadiene and 1,3-cyclooctadiene to a corresponding cyclic monoolefin comprising the step of hydrogenating said diolefin in a hydrogen atmosphere at 50° C. to 200° C. and in the presence of a supported catalyst consisting essentially of from 0.01 to 10% by weight of palladium and from 0.01 to 5% by weight of at least one co-catalyst component selected from the group consisting of ruthenium, rhodium, cobalt, and rhenium said % by weight based on the total weight of the catalyst and support, said support being a non-acidic inorganic compound having a surface area of not more than 100 m$^2$/g, the weight ratio of said co-catalyst metal to the palladium metal being from 0.14 to 5.0.

2. A method according to claim 1 wherein said diolefin is cyclopentadiene and the mol ratio of the diolefin to the molecular hydrogen falls in the range of 1:0.8 to 1.5 and at a temperature of 40° C. to 300° C.

3. The method of claim 1 where there is present 0.05 to 2% by weight palladium and from 0.05% to 1% by weight of the co-catalyst metal.

4. The method of claim 1 where the mol ratio of said diolefin to hydrogen is from about 1 to 0.8 to about 1 to 1.5.

5. The method of claim 1 where the co-catalyst metal is ruthenium.

6. The method of claim 1 wherein said cyclic diolefin is cyclopentadiene.

* * * * *